United States Patent [19]

Green et al.

[11] 4,076,708

[45] Feb. 28, 1978

[54] PROCESS FOR THE PREPARATION OF 7α-HALOGENO-3-OXO-4-DEHYDRO STEROIDS AND NOVEL 7α-HALOGENO DERIVATIVES PRODUCED THEREBY

[75] Inventors: Michael J. Green, Kendall Park; Ho-Jane Shue, Belleville; Elliot L. Shapiro, Cedar Grove; Margaret A. Gentles, Bloomfield, all of N.J.

[73] Assignee: Schering Corporation, Kenilworth, N.J.

[21] Appl. No.: 753,257

[22] Filed: Dec. 22, 1976

[51] Int. Cl.$^2$ .............................................. C07J 71/00
[52] U.S. Cl. .................... 260/239.57; 260/397.45; 260/397.4; 260/239.55 R
[58] Field of Search ................. 260/239.57, 397.45

[56] References Cited

U.S. PATENT DOCUMENTS 3,148,184  9/1964  Gould et al. .................... 260/239.55
3,574,761  4/1971  Uskokovic et al. .................. 260/586

Primary Examiner—Elbert L. Roberts
Attorney, Agent, or Firm—Mary S. King; Stephen B. Coan

[57] ABSTRACT

3-Oxo-6-unsubstituted-7α-halogeno-4-dehydro steroids, wherein said halogen is chlorine, bromine or iodine, are prepared by reaction of a 3-oxo-6,7-di-unsubstituted-4,6-bis-dehydro steroid with at least an equimolar quantity of the corresponding hydrogen halide in a non-reactive organic solvent at temperatures no higher than about 30° C, and then are isolated by removal of said solvent and any excess acid at temperatures no higher than about 25° C without subjecting said 3-oxo-6-unsubstituted-7α-halogeno-4-dehydro steroid to a basic medium.

A preferred species of this process is that wherein the starting steroid is a 3,20-dioxo-9-unsubstituted-11-oxygenated-1,4,6-pregnatriene-17,21-diol or ester thereof, preferably a 17,21-di-lower alkanoate or a 17-benzoate 21-lower alkanoate ester thereof, whereby is prepared in good yields a 3,20-dioxo-7α-halogeno-1,4-pregnadiene-17α,21-diol or ester thereof, useful as topical anti-inflammatory agents.

Also described are novel 3,20-dioxo-7α-halogeno-4-pregnene-17α,21-diols and esters thereof having anti-inflammatory activity as well as 3-oxo-7α-halogeno-17α-4-pregnene-21,17β-carbolactone aldosterone antagonists.

18 Claims, No Drawings

PROCESS FOR THE PREPARATION OF 7α-HALOGENO-3-OXO-4-DEHYDRO STEROIDS AND NOVEL 7α-HALOGENO DERIVATIVES PRODUCED THEREBY

FIELD OF INVENTION

This invention relates to a novel process and to novel compositions-of-matter produced thereby.

More specifically, this invention relates to a process for preparing 3-oxo-6-unsubstituted-7α-halogeno-4-dehydro steroids and to novel steroidal derivatives produced thereby.

In particular, this invention relates to a process for preparing 3-oxo-6-unsubstituted-7α-halogeno-4-dehydro steroids and to novel 3,20-dioxo-6-unsubstituted-7α-halogeno-4-pregnene anti-inflammatory agents and 3-oxo-6-unsubstituted-7α-halogeno-17α-4-pregnene-21,17β-carbolactone aldosterone antagonists produced thereby.

DESCRIPTION OF THE PRIOR ART

Described by P. A. Diassi et al., J. Med. Chem 10, 551–556 (July, 1967) is the reaction of a 2-oxo-6,7-di-unsubstituted-3,6-bis-dehydro A-nor steroid of the A-nor-androstane and A-nor-progesterone series with dichlorodicyanohydroquinone (DDQ) and anhydrous hydrogen chloride in dioxane whereby is produced a 2-oxo-6-unsubstituted-7α-chloro-3-dehydro-A-nor steroid of the A-nor-androstane and A-nor-progesterone series which have no significant hormonal activity.

Also disclosed by Diassi et al is that when the corresponding reaction is carried out on normal steroids (e.g. testosterone or 16α,17α-dimethylmethylenedioxyprogesterone), no 7α-chloro derivative has ever been obtained but, rather, the only isolable product was the corresponding 6-dehydro derivative (e.g. 6-dehydrotestosterone and 6-dehydro-16α,17α-dimethylmethylenedioxyprogesterone).

By our invention, we have developed a process for the preparation and isolation of a 3-oxo-6-unsubstituted-7α-halogeno-4-dehydro steroid by reaction of the corresponding 6,7-di-unsubstituted-4,6-bis-dehydro steroid with a hydrogen halide in a non-reactive solvent, a preferred species of which is the preparation of 3,20-dioxo-7α-halogeno-1,4-pregnadiene-11β,17α,21-triols and 17,21-diesters thereof, which exhibit high topical anti-inflammatory activity.

DESCRIPTION OF THE PROCESS ASPECT OF THE INVENTION

The process aspect of this invention resides in the concept of preparing and isolating a 3-oxo-6-unsubstituted-7α-halogeno-4-dehydro steroid by the reaction of a 3-oxo-6,7-di-unsubstituted-4,6-bis-dehydro steroid with a hydrogen halide in a non-reactive, organic solvent followed by isolation of the 3-oxo-6-unsubstituted-7α-halogeno-4-dehydro steroid thereby formed under conditions which will yield said 3-oxo-6-unsubstituted-7α-halogeno-4-dehydro steroid substantially free of acid or base.

More specifically, the process aspect of this invention resides in the concept of the process for the preparation and isolation of a 3-oxo-6-unsubstituted-7α-halogeno-4-dehydro steroid of the pregnane and 17-spirolactone series wherein said halogen has an atomic weight greater than 20 which comprises the reaction of a 3-oxo-6,7-di-unsubstituted-4,6-bis-dehydro steroid of the pregnane and 17-spirolactone series with at least an equimolar quantity of the corresponding hydrogen halide in a non-reactive, organic solvent at temperatures no higher than about 30° C and thence isolation of the 3-oxo-6-unsubstituted-7α-halogeno-4-dehydro steroid thereby formed at temperatures no higher than about 25° C by removing any excess acid and said solvent without subjecting said 3-oxo-6-unsubstituted-7α-halogeno-4-dehydro steroid to a basic medium, so as to obtain said 3-oxo-6-unsubstituted-7α-halogeno-4-dehydro steroid substantially free of acid or base.

The hydrogen halides useful in our process are those wherein said halide has an atomic weight greater than 20, i.e. hydrogen chloride, hydrogen bromide and hydrogen iodide, whereby are prepared the 7α-chloro, 7α-bromo and 7α-iodo derivatives, respectively.

Our process may be carried out under an inert atmosphere, e.g. argon or nitrogen; however, this is not necessary.

Our process is usually carried out under anhydrous conditions to avoid hydrolysis of any esters present; however, when the reaction time is short (e.g. less than about an hour), water is sometimes advantageously employed to increase the concentration of hydrogen halide in the reaction mixture.

Saturated solutions of hydrogen halide in solvent are preferably employed to minimize reaction time. When carrying out our process, the total molar quantity of hydrogen halide ought be at least equal to the molar quantity of 3-oxo-4,6-bisdehydro steroid, at least a 5-molar excess of hydrogen halide per mole of steroid usually being employed. To insure maximum yields of 3-oxo-7α-halogeno-4-dehydro steroids, we have found it advantageous to utilize from about 10 to about 50 moles of hydrogen halide per mole of steroid.

Solvents suitable for use in this process are any non-reactive organic solvents in which the starting 3-oxo-6,7-di-unsubstituted-4,6-bis-dehydro or 1,4,6-trisdehydro steroids and the hydrogen halide are soluble. By "non-reactive" is meant any organic solvent which will not react with the steroid substrate or the hydrogen halide which would cause transformations resulting in competing side reactions. Thus, in our process, solvents to be avoided are alcohols (which might cause ester exchange under acid conditions) and nitriles such as acetonitrile (which would form iminoethers with steroidal alcohols).

Particularly useful solvents for our hydrogen halide addition process are ethers such as dioxane, tetrahydrofuran and diethyl ether; chlorinated solvents such as chloroform, methylene chloride and 1,2-ethylenedichloride; organic acids such as acetic and propionic acids; tertiary amides such as dimethylformamide, diethylformamide, and hexamethylphosphortriamide; and dimethylsulfoxide.

When carrying out our process, we usually use dioxane, acetic acid or tetrahydrofuran as solvent, tetrahydrofuran being preferred for reactions with hydrogen chloride and acetic acid for reactions with hydrogen bromide or hydrogen iodide.

Our reaction whereby a hydrogen halide is added to a 6-dehydro bond is preferably carried out at temperatures in the range of from about 0° C to about room temperature (e.g. 30° C) although lower temperatures (e.g. −20° C) and temperatures as high as about 60° C may sometimes be employed when preparing a 3-oxo-7α-chloro-1,4-pregnadiene-17α,21-diol- or an ester thereof. The reaction time depends upon the hydrogen halide, solvent, and concentration being employed. Thus, for example, the addition of hydrogen iodide in acetic acid is usually complete within one or two minutes; while the addition reaction utilizing hydrogen bromide in acetic acid at room temperature may require from 20 to 60 minutes for completion. The addition of hydrogen chloride in tetrahydrofuran is preferably carried out at 0° C since greater concentrations of hydrogen chloride in solvent are thereby obtained so that the reaction is completed within an hour. When carried out at room temperature, the addition of hydrogen chloride to a 6-dehydro bond may take up to 24 hours.

The starting compounds of our process may be any 3-oxo-6,7-di-unsubstituted-4,6-bis-dehydro or 1,4,6-trisdehydrosteroid of the pregnane and spirolactone series which are preferably devoid of a halogen at C-9 since the presence of a 9α-halogen appears to inhibit the desired reaction with resulting poor yields of desired 3-oxo-7α,9α-dihalogeno-4-dehydro steroid.

Substituents present in the 3-oxo-4,6-bis-dehydro and 3-oxo-14,6-tridehydro starting steroids of our process usually remain unchanged under the conditions of our process. Indeed, it is usually preferable to have all the substituents desired in the 7α-halogeno-4-dehydro or 1,4-bis-dehydro product present in the 3-oxo-4,6-bisdehydro or 1,4,6-trisdehydro steroid starting compound. Thus, by way of example, the 3,20-dioxo-4,6-pregnadiene and 1,4,6-pregnatriene starting steroids of our process may be substituted at C-2 by methyl or halogen, at C-11 by oxygen, hydroxyl, formyloxy and halogen; at C-16 by acyloxy, alkyl, alkylidene, halogenoalkylidene, halogen; and at C-17 there may be present a corticoid side chain and derivatives thereof, or a progesterone side chain which may be substituted by a 17α-hydroxy-,17α-acyloxy or 17α-halogen and at C-21 by halogen, oxygen, and derivatives thereof.

The 3-oxo-4,6-pregnadiene and 1,4,6-pregnatriene and starting compounds of our process are either known compounds or are conveniently prepared from the corresponding 3-oxo-4-pregnene and 1,4-pregnadiene utilizing techniques known to effect dehydrogenation between C-6 and C-7 such as those utilizing chloranil or 2,3-dichloro-5,6-dicyanobenzoquinone (DDQ) or by bromination at C-6 followed by dehydrobromination. Since ester groups are usually present in the starting steroid, anhydrous conditions are preferably employed to minimize the possibility of hydrolysis.

The 3-oxo-4,6-diene starting compounds of the 17-spirolactone series, e.g. 3-oxo-17α-4,6-pregnadiene-21,17β-carbolactone, are known compounds. The 3-oxo-1,4,6-triene starting compounds of the 17-spirolactone series are either known compounds or are conveniently prepared from the corresponding 3-oxo-4,6-diene utilizing techniques known to effect dehydrohalogenation between C-1 and C-2 such as those utilizing DDQ in refluxing benzenedioxane.

The preferred mode of our process is that wherein a 6-dehydro derivative of a 3,20-dioxo-6,7-di-unsubstituted-1,4-pregnadiene having anti-inflammatory activity is reacted with a hydrogen halide wherein said halide has an atomic weight greater than 20, in a non-reactive, organic solvent at temperatures usually no greater than about 30° C whereby is obtained, in good yields, the corresponding 3,20-dioxo-7α-halogeno-1,4-pregnadiene having anti-inflammatory activity, said 7α-halogeno-1,4-pregnadienes being described and claimed in copending application Ser. No. 753,256, filed concurrently with this application, of Michael J. Green and Ho-Jane Shue for 7α-Halogeno-3,20-Dioxo-1,4-Pregnadienes, Methods for their Manufacture, Their Use as Anti-inflammatory Agents, and Pharmaceutical Formulations Useful Therefor, the disclosure therein being incorporated herein by reference.

A particularly valuable mode of our process is that shown in following Chart A wherein a 3-oxo-6,7,9-triunsubstituted-1,4,6-pregnatriene of formula I is reacted with a hydrogen halide, preferably hydrogen chloride or hydrogen bromide, in a non-reactive, organic solvent at temperatures no higher than about 30° C to obtain a 3-oxo-7α-halogeno-1,4-pregnadiene of formula II

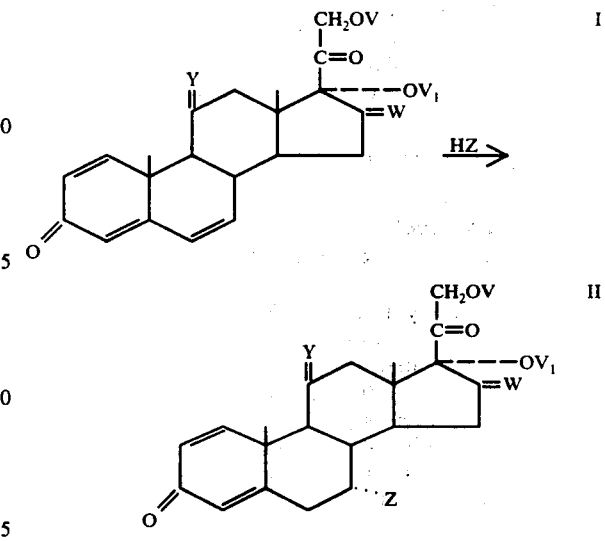

wherein
Y is oxo or (H,βOH);
W is (H,H); (H,CH$_3$) or =CH$_2$;
V and V$_1$ are each hydrogen or an acyl radical of a hydrocarboncarboxylic acid having up to 12 carbon atoms; and
Z is chlorine, bromine, or iodine.

The acyl radicals of the compounds of formulae I and II as defined by V and V$_1$ hereinabove, include those derived from hydrocarboncarboxylic acids having up to 12 carbon atoms which may be saturated, unsaturated, straight chain or branched chain, aliphatic, cyclic, cyclic-aliphatic, aromatic, aryl-aliphatic, or alkyl-aromatic, and may be substituted by hydroxy, alkoxy containing from 1 to 5 carbon atoms or by a halogen. Typical ester groups are thus derived from hydrocarboncarboxylic acids such as alkanoic acids exemplified by formic, acetic, propionic, trimethylacetic, butyric, isobutyric, valeric, isovaleric, caproic, tert.-butylacetic, enanthic, caprylic, capric, cyclopentylpropionic, undecylic, lauric, and adamantanecarboxylic acids; substituted alkanoic acids such as phenoxyacetic, trifluoroacetic, and β-chloropropionic acids; aromatic and substituted aromatic acids including benzoic, toluic, p-chlorobenzoic, p-fluorobenzoic, p-methoxybenzoic, and 3',5'-dimethylbenzoic acids; aryl-alkanoic acids such as phenylacetic, phenylpropionic, and β-benzoylaminoisobutyric acids; unsaturated acids such as acrylic and sorbic acids; and dibasic acids such as succinic, tartaric, phthalic and benzene disulfonic acids.

Preferred hydrocarboncarboxylic esters are the lower alkanoyloxy esters which are contemplated as including acid radicals of lower alkanoic acids having preferably up to 8 carbon atoms such as radicals obtained from acetic, propionic, butyric, valeric, caprylic, caproic,tert.-butylacetic acid and the like. Other preferred hydrocarboncarboxylic esters include those derived from benzoic acid or substituted benzoic acids.

The process illustrated in Chart A hereinabove is a preferred mode of our invention since the compounds of formula II produced thereby are very useful as topical anti-inflammatory agents, especially those wherein V and $V_2$ are acyl radicals of hydrocarboncarboxylic acids having up to 8 carbon atoms, particularly the 17-propionate, 17-n-butyrate- and 17-benzoate-derivatives which exhibit high topical anti-inflammatory activity with a minimum of systemic corticoid effects. Particularly valuable compounds of formula II prepared by our process are 7α-chloro- and 7α-bromo-16α-methyl-1,4-pregnadiene-11β,17α,21-triol-3,20-dione 17,21-dipropionate and the corresponding 17-benzoate 21-acetate.

Generally, when carrying out the preferred mode of our process whereby a hydrogen halide is added to a 6-dehydro bond, to a saturated solution of dry hydrogen halide in anhydrous solvent (e.g. hydrogen bromide in acetic acid) usually at 0° to 20° C, is added the starting 3,20-dioxo-1,4,6-pregnatriene (e.g. 16α-methyl-1,4,6-pregnatriene-11β,17α,21-triol-3,20-dione 17-benzoate 21-acetate) either in the solid state or in solution, the molar quantity of hydrogen halide to steroid being about 40 to 1. After the reaction is complete, as determined by thin layer chromatography, the 7α-halogeno-3,20-dioxo-1,4-pregnadiene thereby produced is conveniently isolated by pouring the reaction mixture into ice water and separating the resultant precipitate of 7α-halogeno-3,20-dioxo-1,4-pregnadiene (e.g. 7α-bromo-16α-methyl-1,4-pregnadiene-11β,17α,21-triol-3,20-dione 17-benzoate 21-acetate) via filtration or extraction techniques followed by purification utilizing known techniques, usually via chromatography.

To insure maximum yields of pure products we have found it necessary to usually carry out the reaction and isolation steps at temperatures no higher than about 25° C, and to avoid the use of a basic medium during the isolation step.

After isolation, the 7α-halogeno-1,4-pregnadienes are preferably kept at cool temperatures (e.g. 0° to 5° C) to minimize decomposition. For short term storage, the 7α-chloro derivatives are relatively stable up to 100° C; however, the 7α-bromo-1,4-pregnadienes are preferably kept below 55° C.

We have found, when preparing a 7α-halogeno-11β-hydroxy-3,20-dioxo-1,4-pregnadiene of formula II by the aforedescribed process, that better overall yields of pure product are obtained over that produced from the corresponding 11β-hydroxy-3,20-dioxo-1,4-pregnadiene when one hydrohalogenates the corresponding 11-oxo intermediate followed by reduction of the resulting 7α-halogeno-3,11,20-trioxo-1,4-pregnadiene with sodium borohydride (e.g. in methanol) whereby, when a 17-acyloxy group is present and when any 21-hydroxyl function is also esterified, there is obtained the corresponding 7α-halogeno-3,20-dioxo-11β-oL without reduction at the 3- or 20-oxo function. Thus, a preferred method of preparing 7α-chloro-16α-methyl-1,4-pregnadiene-11β,17α,21-triol-3,20-dione 17,21-dipropionate comprises reaction of 16α-methyl-1,4,6-pregnatriene-17α,21-diol-3,11,20-trione 17,21-dipropionate with anhydrous hydrogen chloride in tetrahydrofuran at 0° C followed by reduction of the thereby formed 7α-chloro-16α-methyl-1,4-pregnadiene-17α,21-diol-3,11,20-trione 17,21-dipropionate with sodium borohydride in methanol to produce excellent yields of pure 7α-chloro-16α-methyl-1,4-pregnadiene-11β,17α,21-triol-3,20-dione 17,21-dipropionate.

Another mode of our process is that wherein the starting steroid is a 6-dehydro derivative of a 3-oxo-6,7-di-unsubstituted-4-pregnene having anti-inflammatory activity whereby is obtained the corresponding 3-oxo-6-unsubstituted-7α-halogeno-4-pregnene anti-inflammatory agent. A preferred species of this aspect of our process is that wherein a 1,2-dihydro analog of formula I (Chart A) is reacted with a hydrogen halide in a non-reactive solvent at temperatures less than about 30° C whereby is obtained a 1,2-dihydro analog of formula II, said compounds possessing anti-inflammatory activity and being a composition-of-matter aspect of this invention disclosed further hereinbelow.

When the starting compound is a 1,2-dihydro-4,6-pregnadiene, e.g. a 1,2-dihydro analog of formula I such as 4,6-pregnadiene-11β,17α,21-triol-3,20-dione 17,21-dipropionate, the manner in which the process is carried out is essentially the same as when the starting steriod is a 1,4,6-pregnatriene. We have found, however, that the conversion of a 3,20-dioxo-7α-halogeno-4-pregnene proceeds at a faster rate so that the reaction can be carried out in the presence of water without hydrolyzing to any great extent ester groups which may be present. Additionally, we have discovered the 1,2-dihydro analogs of the 7α-halogeno corticoids of formula II are much less stable than their 1,2-dehydro analogs so that it is necessary to isolate the product from the excess acid as quickly as possible without using a basic medium and to store the 3,20-dioxo-7α-halogeno-1,2-dihydro compound of formula II in vacuo in an open vessel at temperatures no higher than about 25° C. We have also found when preparing a 3-oxo-7α-halogeno-11β-hydroxy-1,2-dihydro-4-pregnene by reduction of the corresponding 11-oxo derivative with sodium borohydride, that better yields of desired product are obtained when the resultant 7α-halogeno-11β-hydroxy product is treated with manganese dioxide at room temperature prior to purification via chromatographic techniques.

Another mode of the process aspect of our invention is that wherein spirolactones of following formulae III and IV are prepared by the reaction of the corresponding 7-unsubstituted-6-dehydro derivative with a hydrogen halide in a non-reactive, organic solvent at temperatures no higher than about 30° C

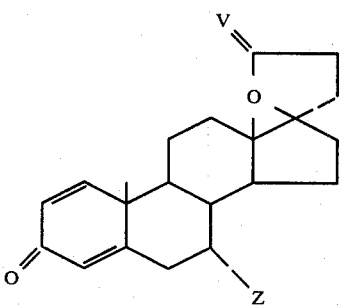

III

-continued

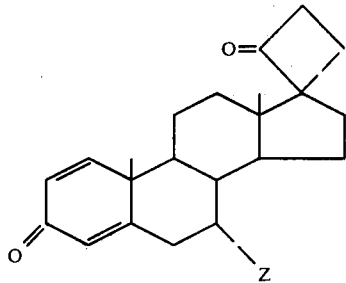

IV wherein Z is a halogen having an atomic weight greater than 20 and V is oxygen or hydrogen, and the 1,2-dihydro analogs thereof.

The 7α-halogeno-1,4-bis-dehydro compounds of formulae III and IV are described and claimed in copending application Ser. No. 753,258, filed on the same date as the instant application, of Michael J. Green and Ho-Jane Shue for 7α-Halogeno-3-Oxo-1,4-Pregnadiene-21,17β-Carbolactones and Related Compounds, the disclosure therein being incorporated herein by reference.

The 7α-halogeno-1,2-dihydro analogs of formulae III and IV are novel compounds of this invention which are discussed hereinbelow under the composition-of-matter aspect of the invention.

THE COMPOSITION-OF-MATTER ASPECT OF THE INVENTION

A composition-of-matter aspect of this invention resides in the concept of a 3,20-dioxo-7α-halogeno-4-pregnene having cortical activity, particularly 7α-halogeno-4-pregnene-11β,17α,21-triol-3,20-dione 17,21-dihydrocarboncarboxylates, which exhibit topical anti-inflammatory activity.

Typical 7α-halogeno-4-pregnenes of our invention include 3,20-dioxo-7α-halogeno-4-pregnenes of following formula V:

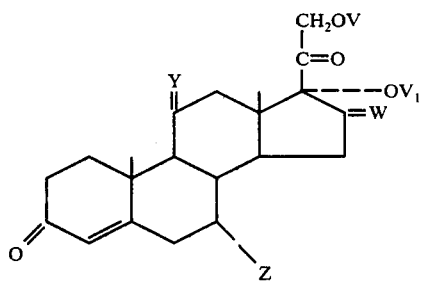

V wherein
Y is oxo or (H,βOH);
W is (H,H); (H,CH₃) or =CH₂;
V and V₁ are each hydrogen or an acyl radical of a hydrocarboncarboxylic acid having up to 12 carbon atoms; and
Z is a halogen having an atomic weight greater than 20.

As used in the specification and claims of this application, the term "acyl" denotes a radical derived from an acid by removal of a hydroxyl group; e.g. acetyl is the acyl radical of acetic acid, benzenesulfonyl is the acyl radical of benzenesulfonic acid, and benzoyl is the acyl radical of benzoic acid.

The acyl radicals of the compounds of this invention as defined by V and V₁ in formula V hereinabove include those derived from hydrocarboncarboxylic acids having up to 12 carbon atoms and are of the same scope as that set forth hereinabove with reference to compounds to formulae I and II.

Of the 7α-halogeno-3,20-dioxo-4-pregnenes of formula V, preferred are the 7α-chloro and 7α-bromo derivatives, particularly those wherein Y is (H,βOH).

The 7α-halogeno-3,20-dioxo-4-pregnenes of formula V exhibit topical anti-inflammatory activity and thus are useful in the treatment of all corticosteroid-responsive dermatoses such as contact and allergic dermatitis and psoriasis. They may be applied topically or locally in any of the conventional pharmaceutical forms provided they are free of acid or base, which are prepared according to procedures well known in the art.

The 11-oxo derivatives of formula I (i.e. those wherein Y is oxygen), while possessing anti-inflammatory activity, are more frequently used as intermediates in the preparation of the corresponding 11β-hydroxy derivatives prepared according to procedures disclosed hereinabove and in the Examples.

Of the compounds of formula V, preferred as topical anti-inflammatory agents are those wherein V and V₁ are acyl radicals of hydrocarboncarboxylic acids having up to 8 carbon atoms, particularly the 17-propionate, 17-n-butyrate and 17-benzoate derivatives including 17-monoesters and 17,21-di-esters.

Preferred compounds of formula V include the 21-acetate, 21-propionate, 21-n-butyrate, 21-isobutyrate and the 21-valerate ester derivatives of 7α-chloro-16α-methyl-4-pregnene-11β,17α,21-triol-3,20-dione 17-propionate, and the 21-acetate, 21-propionate, 21-n-butyrate and 21-isobutyrate ester derivatives of 7α-bromo-16α-methyl-4-pregnene-11β,17α,21-triol-3,20-dione 17-propionate;

the 21-acetate, 21-propionate, and 21-n-butyrate ester derivatives of 7α-bromo-16α-methyl-4-pregnene-11β,17α,21-triol-3,20-dione 17-n-butyrate, and the 21-acetate, 21-propionate and 21-n-butyrate ester derivatives of 7α-chloro-16α-methyl-4-pregnene-11β,17α,21-triol-3,20-dione 17-n-butyrate;

the 21-acetate, 21-propionate, 21-n-butyrate and 21-benzoate ester derivatives of 7α-chloro-16α-methyl-4-pregnene-11β,17α,21-triol-3,20-dione 17-benzoate, and the corresponding 7α-bromo derivatives.

Other compounds of formula V include:
7α-chloro-16α-methyl-4-pregnene-11β,17α,21-triol-3,20-dione 17-valerate 21-acetate, and the corresponding 7α-bromoderivative;

7α-chloro-16α-methyl-4-pregnene-11β,17α,21-triol-3,20-dione 17-isobutyrate 21-acetate and the corresponding 7α-bromo derivative thereof;

7α-chloro-16α-methyl-4-pregnene-11β,17α,21-triol-3,20-dione and the 21-acetate, 21-benzoate, 21-pivalate, 17-propionate and 17-valerate thereof and the corresponding 7α-bromo derivative;

the 16β-methyl epimers of the above-named 16α-methyl derivatives such as the 21-acetate, the 17,21-dipropionate, the 17-propionate 21-n-butyrate, the 17-propionate 21-acetate, the 17-benzoate 21-acetate of 7α-chloro-16β-methyl-4-pregnene-11β,17α,21-triol-3,20-dione and of the corresponding 7α-bromo derivative thereof;

and 16-methylene derivatives such as 7α-chloro-16-methylene-4-pregnene-11β,17α,21-triol-3,20-dione 17,21-dipropionate.

In addition to the preferred compounds of formula V, our invention includes 16-unsubstituted-7α-halogeno-3,20-dioxo-4-pregnene analogs of the aforenamed 16α-methyl-, 16β-methyl-, and 16-methylene derivatives, e.g. 7α-chloro-4-pregnene-11β,17α,21-triol-3,20-dione 17,21-dipropionate.

The physical embodiments of the 7α-halogeno-3,20-dioxo-4-pregnenes of formula V are characterized by being crystal-line solids, usually white to off-white in color, which are insoluble in water and soluble in most organic solvents, particularly in acetone, dioxane, dimethylformamide, and dimethylsulfoxide, although of limited solubility in non-polar solvents such as dialkyl ethers and alkyl hydrocarbons.

The 7α-halogeno-3,20-dioxo-4-pregnenes of formula V are preferably stored in an open vessel in vacuo at cool temperatures (e.g. 0° to 40° C) to minimize decomposition to the corresponding 4,6-pregnadiene starting compound with release of hydrogen halide. We have also discovered that when the 3,20-dioxo-7α-halogeno-4-pregnenes of formula II are dissolved in methanol, the rate of decomposition is diminished.

Another composition-of-matter aspect of this invention resides in the concept of 7α-halogeno derivatives of 3-oxo-17α-4-pregnene-21,17β-carbolactone, 2′,3′α-tetrahydrofuran-2′-spiro-17(4-androstene-3one) and (17R)-spiro-[4-androstene-17,1′-cyclobutane]-3,2′-dione, preferably 7α-chloro- and 7α-bromo-derivatives having aldosterone activity.

Thus, included within our invention are 7α-halogeno derivatives of following formulae VI and VII:

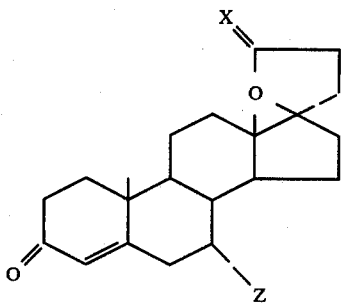

VI

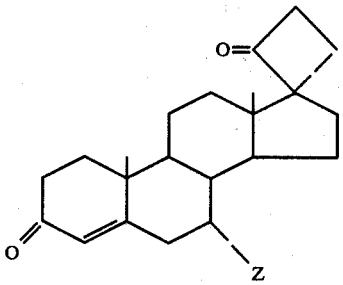

VII wherein Z is halogen of atomic weight less than 20, and Z is oxygen or hydrogen.

The halogens at C-7 as defined by Z include chlorine, bromine, and iodine. Of these, preferred are chlorine and bromine.

Our invention thus includes 7α-halogeno derivatives of formula VI wherein Z is oxygen, i.e.
3-oxo-7α-chloro-17α-4-pregnene-21,17α-carbolactone,
3-oxo-7α-bromo-17α-4-pregnene-21,17β-carbolactone, and
3-oxo-7α-iodo-17α-4-pregnene-21,17β-carbolactone;

7α-halogeno derivatives of formula VI wherein Z is hydrogen, i.e.
2′,3′α-tetrahydrofuran-2′-spiro-17(7α-chloro-4-androstene-3-one),
2′,3′α-tetrahydrofuran-2′-spiro-17(7α-bromo-4-androstene-3-one), and
2′,3′α-tetrahydrofuran-2′-spiro-17(7α-iodo- 4-androstene-3-one);

7α-halogeno derivatives of formula VII, i.e.
(17R)-spiro-[7α-chloro-4-androstene-17,1′-cyclobutane]-3,2′-dione,
(17R)-spiro-[7α-bromo-4-androstene-17,1′-cyclobutane]-3,2′dione, and
(17R)-spiro-[7α-iodo-4-androstene-17,1′-cyclobutane]-3,2′-dione.

Of the foregoing, preferred are the 7α-halogeno pregnene-21,17β-carbolactones of formula VI wherein Z is oxygen, particularly the 7α-chloro and 7α-bromo derivatives.

The 7α-halogeno compounds of formulae VI and VII exhibit aldosterone antagonist activity and, as such, are useful in the treatment of primary aldosteronism and as diuretic agents especially in the treatment of hepatic cirrhosis and in nephrotic syndrome. Also, they are useful in treating various types of hypertension and in congestive heart failure. The aldosterone antagonists are usually administered orally or parenterally in effective doses dependent upon the nature and severity of the ailment and on the age and weight of the patient.

The process described hereinabove is illustrated in detail in the Examples hereinbelow and should not be construed as limiting the scope of the invention, equivalents thereof and products produced thereby which will be obvious to one skilled in the art, being considered a part of the invention.

PREPARATION 1

16α-Methyl-1,4,6-Pregnatriene-11β,17α,21-Triol-3,20-Dione and 21-Esters Thereof

A. 16α-Methyl-1,4,6-Pregnatriene-11β,17α,21-Triol-3,20-Dione 21-Acetate

To a solution of dry hydrogen chloride gas (22 gms.) in dioxane (660 ml.), add 16α-methyl-1,4-pregnadiene-11β,17α,21-triol-3,20-dione 21-acetate (10 gms.) followed by 2,3-dichloro-5,6-dicyanobenzoquinone (DDQ) (6.55 gms.) and stir at room temperature for 24 hours. Filter the reaction mixture and evaporate the filtrate at 40° C in vacuo. Dissolve the resultant residue in chloroform:ethyl acetate (1:1) and filter the solution through a column of neutral alumina, washing the column with the same solvent system. Evaporate the eluates and crystallize the resultant residue from methanol:hexane to give 16α-methyl-1,4,6-pregnatriene-11β,17α,21-triol-3,20-dione 21-acetate.

B. 16α-Methyl-1,4,6-Pregnatriene-11β,17α,21-Triol-3,20-Dione

To a solution of 16α-methyl-1,4,6-pregnatriene-11β,17α,21-triol-3,20-dione 21-acetate (1.5gms.) in methanol (360 ml.) add saturated aqueous sodium bicarbonate solution (40 ml.). Stir at room temperature for 2 hours, then filter and evaporate in vacuo. Dissolve the resultant residue in ethyl acetate, wash the ethyl acetate solution with water, dry over magnesium sulfate and evaporate in vacuo to obtain 16α-methyl-1,4,6-pregnatriene-11β,17α,21-triol-3,20-dione.

C. 16α-Methyl-1,4,6-Pregnatriene-11β,17α,21-Triol-3,20-Dione 21-Benzoate

1. To 16α-methyl-1,4,6-pregnatriene-11β,17α,21-triol-3,20-dione (0.68 gms.) in pyridine (6.12 ml.) add benzoyl chloride (1.36 ml.). Stir at room temperature for 30 minutes, then pour with aqueous saturated sodium bicarbonate solution, then with water, then dry over magnesium sulfate and evaporate in vacuo to a residue of 16α-methyl-1,4,6-pregnatriene-11β,17α,21-triol-3,20-dione 21-benzoate.

2. In the above procedure, by substituting for benzoyl chloride equivalent quantities of substituted benzoyl chloride, e.g. p-toluyl chloride, p-fluorobenzoyl chloride and 3',5'-di-methylbenzoyl chloride, there is obtained the corresponding 21-substituted benzoate ester, e.g. the 21-p-toluate, 21-p-fluorobenzoate and 21-(3',5'-dimethylbenzoate) of 16α-methyl-1,4,6-pregnatriene-11β,17α,21-triol-3,20-dione.

D. 16α-Methyl-1,4,6-Pregnatriene-11β,17α,21-Triol-3,20-Dione 21-Hydrocarboncarboxylates 1. 16α-Methyl-1,4,6-Pregnatriene-11β,17α,21-Triol-3,20-Dione 21-Trimethylacetate:

To 16α-methyl-1,4,6-pregnatriene-11β,17α,21-triol-3,20-dione (0.4 gms.) in pyridine (3 ml.) at 0° C, add dropwise a solution of trimethylacetyl chloride (0.4 ml.) in pyridine (1 ml.). Allow the reaction mixture to warm to room temperature, then leave at room temperature for 30 minutes. Pour the reaction mixture into water (250 ml.), extract the aqueous mixture with ethyl acetate, then wash the organic extracts successively with 1 N hydrochloric acid, aqueous saturated sodium bicarbonate, then water. Dry over magnesium sulfate and evaporate in vacuo to a residue of 16α-methyl-1,4,6-pregnatriene-11β,17α,21-triol-3,20-dione 21-trimethylacetate.

2. In the above procedure, by substituting for trimethylacetyl chloride, equivalent quantities of other hydrocarboncarboxylic acid chlorides, e.g. propionyl chloride, dodecanoyl chloride, valeryl chloride, n-butyryl chloride, cyclopentylpropionyl chloride, cyclohexylcarbonyl chloride, 1-adamantylacetyl chloride, and 1-adamantylcarboxylic acid chloride, there is obtained the corresponding 21-hydrocarboncarboxylate ester, e.g. the 21-propionate, 21-dodecanoate, 21-valerate, 21-n-butyrate, 21-cyclopentylpropionate, 21-cyclohexanecarboxylate, 21-(1'-adamantylacetate) and 21-(1'-adamantylcarboxylate) of 16α-methyl-1,4,6-pregnatriene-11β,17α,21-triol-3,20-dione.

PREPARATION 2

16α-Methyl-1,4,6-Pregnatriene-11β,17α,21-Triol-3,20-Dione 17-Lower Alkanoates and 17,21-Alkylorthoalkanoates A. 16α-Methyl-1,4,6-Pregnatriene-11β,17α,21-Triol-3,20-Dione 17-Propionate 1. 16β-Methyl-1,4,6-Pregnatriene-11β,17α,21-Triol-3,20-Dione 17,21-Ethylorthopropionate:

To 16α-methyl-1,4,6-pregnatriene-11β,17α, 21-triol-3,20-dione (1.9 gms.) in dimethylsulfoxide (9.5 ml.), add triethylorthopropionate (3.8 ml.) and p-toluenesulfonic acid monohydrate (0.142 gms.). Stir for 2 hours at room temperature, then pour into water (250 ml.), add saturated aqueous sodium bicarbonate (150 ml.) and extract with ethyl acetate. Combine the ethyl acetate extracts and wash with water, dry over magnesium sulfate and evaporate in vacuo to a residue comprising 16α-methyl-1,4,6-pregnatriene-11β,17α,21-triol-3,20-dione 17,21-ethylorthopropionate.

2. Dissolve the product of Preparation 2A(1) in glacial acetic acid (15 ml.) and water (0.3 ml.). Allow to stand for 1 hour at room temperature, then pour into water (300 ml.) and add an 8% aqueous sodium hydroxide solution (50 ml.). Separate the resultant precipitate by filtration, wash with water and dry at room temperature to give 16α-methyl-1,4,6-pregnatriene-11β,17α, 21-triol-3,20-dione 17-propionate. Further purify by recrystallization from acetone/hexane.

B. 16α-Methyl-1,4,6-Pregnatriene-11β, 17α,21-Triol-3,20-Dione 17-Lower alkanoates 1. 16α-Methyl-1,4,6-Pregnatriene-11β,17α,21-Triol-3,20-Dione 17,21-Alkylorthoalkanoate:

In the procedure of Preparation 2A(1), substitute for triethylorthopropionate the following trialkylorthoalkanoates, e.g. triethylorthoacetate, triethylortho-n-butyrate, triethylorthiosobutyrate and tri-n-butylorthovalerate to obtain the corresponding 17,21-alkylorthoalkanoate, e.g. the 17,21-ethylorthoacetate, the 17,21-ethylortho-n-butyrate, the 17,21-ethylorthoisobutyrate, and the 17,21-n-butylorthovalerate, respectively of 16α-methyl-1,4,6-pregnatriene-11β,17α,21-triol-3,20-dione.

2. 16α-Methyl-1,4,6-Pregnatriene-11β,17α,21-Triol-3,20-Dione 17-Lower alkanoate

Treat each of the 17,21-alkylorthoalkanoates prepared in Preparation 2B(1) with aqueous acetic acid in the manner of Preparation 2A(2) to obtain, respectively, the 17-acetate, 17-n-butyrate, 17-isobutyrate, and 17-valerate esters of 16α-methyl-1,4,6-pregnatriene-11β,17α, 21-triol-3,20-dione.

C. 16α-Methyl-1,4,6-Pregnatriene-11β,17α,21-Triol-3,20-Dione 17-Benzoate 1. 16α-Methyl-1,4,6-Pregnatriene-11β,17α,21-Triol-3,20-Dione 17,21-Methylorthobenzoate:

To a solution of 16α-methyl-1,4,6-pregnatriene-11β,17α,21-triol-3,20-dione (1 gm.) in dioxane (56 ml.) and benzene (84 ml.) add pyridinium p-toluenesulfonate (0.25 gms.) and trimethylorthobenzoate (1.5 ml.). Heat the reaction mixture at reflux temperature for 2 days, then add additional pyridinium p-toluenesulfonate (0.1 gms.) and trimethylorthobenzoate (1 ml.). Heat at reflux temperature an additional 3 days, then again add additional pyridinium p-toluenesulfonate (0.1 gms.) and trimethylorthobenzoate (1 ml.). Heat at reflux temperature another 3 days, cool, add pyridine (0.45 ml.) and evaporate in vacuo. Dissolve the resultant residue in ethyl acetate, wash the ethyl acetate solution with water, dry over magnesium sulfate and evaporate to a residue comprising 16α-methyl-1,4,6-pregnatriene-11β,17α,21-triol-3,20-dione 17,21-methylorthobenzoate.

In the above procedure by substituting for trimethylorthobenzoate an equivalent quantity of trimethylortho-(p-fluorobenzoate) there is obtained 16α-methyl-1,4,6-pregnatriene-11β,17α,21-triol-3,20-dione 17,21-methylortho-(p-fluorobenzoate).

2. Treat 16α-methyl-1,4,6-pregnatriene-11β,17α,21-triol-3,20-dione 17α,21-methylorthobenzoate in aqueous acetic acid in a manner similar to that described in Preparation 2A(2) and isolate the resultant product in a manner similar to that described to obtain 16α-methyl-1,4,6-pregnatriene-11β,17α,21-triol-3,20-dione 17-benzoate.

In similar manner, by treating 16α-methyl-1,4,6-pregnatriene-11β,17α,21-triol-3,20 dione 17α,21-methylortho-(p-fluorobenzoate) with aqueous acetic acid, there is obtained 16α-methyl-1,4,6-pregnatriene-11β,17α,21-triol-3,20-dione 17-p-fluorobenzoate.

PREPARATION 3

16α-Methyl-1,4,6-Pregnatriene-11β,17α,21-Triol-3,20Dione 17,21-Dihydrocarboncarboxylic Acids Ester A. 16α-Methyl-1,4,6-Pregnatriene-11β,17α,21-Triol-3,20-Dione 17-Propionate 21-Alkanoate 1. 16α-Methyl-1,4,6-Pregnatriene-11β,17α,21-Triol-3,20-Dione 17,21-Dipropionate:

To 16α-methyl-1,4,6-pregnatriene-11β,17α,21-triol-3,20-dione 17-propionate (2.8 gms.) in pyridine (23 ml.), add propionic acid anhydride (4.6 ml.) and allow to stand at room temperature for 3.5 hours. Pour into water (250 ml.) containing 1 N hydrochloric acid (50 ml.). Extract with ethyl acetate (100 ml.), wash the combined organic extracts with water, dry over magnesium sulfate and evaporate in vacuo. Chromatograph the resultant residue on a silica gel column eluting with chloroform:ethyl acetate (4:1). Evaporate the combined eluates to a residue comprising 16α-methyl-1,4,6-pregnatriene-11β,17α,21-triol-3,20-dione 17,21-dipropionate.

2. In the procedure of Preparation 3A(1) by substituting for propionic acid anhydride equivalent quantities of other alkanoic anhydrides, e.g. acetic anhydride, n-butyric anhydride, isobutyric anhydride, caprylic acid anhydride and valeric anhydride, there is obtained the corresponding 17-propionate 21-alkanoate ester, e.g. the 17-propionate 21-acetate, 17-propionate 21-n-butyrate, 17-propionate 21-isobutyrate, 17-propionate 21-caprylate, and 17-propionate 21-valerate of 16α-methyl-1,4,6-pregnatriene-11β,17α,21-triol-3,20-dione.

3. Treat 16α-methyl-1,4,6-pregnatriene-11β,17α,21-triol-3,20-dione 17-propionate with benzoyl chloride in a manner similar to that described in Preparation 1C(1) to obtain 16α-methyl-1,4,6-pregnatriene-11β,17α,21-triol-3,20-dione 17-propionate 21-benzoate.

In the above procedure, by substituting for benzoyl chloride equivalent quantities of substituted benzoyl chloride, e.g. p-toluyl chloride, p-fluorobenzoyl chloride and 3', 5'-dimethylbenzoyl chloride, there is obtained the 21-substituted benzoate ester, e.g. the 17-propionate 21-p-toluate, 17-propionate 21-p-fluorobenzoate, and the 17-propionate 21-(3', 5'-dimethylbenzoate) of 16α-methyl-1,4,6-pregnatriene-11β, 17α, 21-triol-3,20-dione.

B. 16α-Methyl-1,4,6-Pregnatriene-11β, 17α, 21-Triol-3,20-Dione 17,21-Dihydrocarboncarboxylates 1. In a manner similar to that described in Preparation 3A(1), treat each of the 17-acetate, the 17-n-butyrate, the 17-isobutyrate, the 17-valerate, and the 17-benzoate esters of 16α-methyl-1,4,6-pregnatriene-11β, 17α, 21-triol-3,20-dione in pyridine with each of the following alkanoic acid anhydrides: acetic anhydride, propionic anhydride, n-butyric anhydride, isobutyric anhydride and valeric anhydride. Isolate and purify each of the resultant products in a manner similar to that described to obtain the corresponding 21-alkanoate of each of the 16α-methyl-1,4,6-pregnatriene-11β, 17α, 21-triol-3,20-dione 17-monoester starting compounds.

2. In a manner similar to that described in Preparation 1C treat each of the 16α-methyl-1,4,6-pregnatriene-11β, 17α, 21-triol-3,20-dione 17-monoester starting compounds of Preparation 3B(1) in pyridine with each of benzoyl chloride, p-toluyl chloride, p-fluorobenzoyl chloride and 3', 5'-dimethylbenzoyl chloride to obtain the corresponding 21-benzoate or substituted benzoate ester, i.e. the 21-benzoate, 21-p-toluate, 21-p-fluorobenzoate, and 21-(3', 5'-dimethylbenzoate) of each of the 16α-methyl-1,4,6-pregnatriene-11β, 17α, 21-triol-3,20-dione 17-monoester starting compounds.

PREPARATION 4

The 17-Esters, 21-Esters, and 17,21-Diesters of 16β-Methyl-1,4,6-Pregnatriene-11β, 17α, 21-Triol-3,20-Dione and of 16α-Methyl-1,4,6-Pregnatriene-17α, 21-Diol-3,11,20-Trione and the 16β-Methyl Epimers Thereof 1. In the procedure of Preparation 1A utilizing as starting compound 16β-methyl-1,4-pregnadiene-11β, 17α, 21-triol-3,20-dione 21-acetate, there is obtained 16β-methyl-1,4,6-pregnatriene-11β, 17α, 21-triol-3,20-dione 21-acetate which, when carried through the sequence of reactions described in Preparations 1–3, will produce the 16α-methyl epimers of the 16α-methyl products described therein.

2. In similar manner, in the procedure of Preparation 1A, by utilizing as starting compound 16α-methyl-1,4-pregnadiene-17α, 21-diol-3,11,20-trione 21-acetate, there is obtained 16α-methyl-1,4,6-pregnatriene-17α, 21-diol-3,11,20-trione 21-acetate which, when carried through the sequence of reactions described in Preparations 1–3, will produce 11-oxo-16α-methyl pregnatriene derivatives corresponding to the 11β-hydroxy-16α-methyl pregnatriene products named therein.

3. In the procedure of Preparation 1A, by utilizing as starting compound 16β-methyl-1,4-pregnadiene-17α, 21-diol-3,11,20-trione 21-acetate, there is obtained 16β-methyl-1,4,6-pregnatriene-17α, 21-diol-3,11,20-trione 21-acetate which, then carried through the sequence of reactions described in Preparations 1–3, will produce the 11-oxo-16β-methyl-pregnatriene derivatives corresponding to the 11β-hydroxy-16α-methyl pregnatriene products named therein.

PREPARATION 5

16-Methylene-1,4,6-Pregnatriene-11β, 17α, 21-Triol-3,20-Dione 21-Propionate and 17,21-Dipropionate A. 16-Methylene-1,4-Pregnadiene-11β, 17α, 21-Triol-3,20-Dione 21-Propionate In a manner similar to that described in Preparation 3A(1), treat 16-methylene-1,4-pregnadiene-11β, 17α, 21-triol-3,20-dione (5 gms.) in pyridine (100 ml.) with propionic acid anhydride (10 ml.). Isolate and purify the resultant product in a manner similar to that described to obtain 16-methylene-1,4-pregnadiene-11β, 17α, 21-triol-3,20-dione 21-propionate.

B. 16-Methylene-1,4-Pregnadiene-11β,17α,21-Triol-3,20-Dione-11-Trifluoroacetate 21-Propionate To a solution of 16-methylene-1,4-pregnadiene-11β,17α,21-triol-3,20-dione 21-propionate (1 gm.) in pyridine (10 ml.) cool to −23° C, add trifluoroacetic anhydride (1 ml.) precooled to −23° C. Allow the reaction mixture to stand at −23° C for 40 minutes, then pour into ice water (200 ml.) containing concentrated hydrochloric acid (8.8 ml.). Separate the resultant precipitate by filtration, wash with water and dry to give 16-methylene-1,4-pregnadiene-11β,17α,21-triol-3,20-dione 11-trifluoroacetate 21-propionate.

C. 16-Methylene-1,4-Pregnadiene-11β,17α,21-Triol-3,20-Dione-11-Trifluoroacetate 17,21-Dipropionate To a solution of 16-methylene-1,4-pregnadiene-11β,17α,21-triol-3,20-dione 11-trifluoroacetate 21-propionate (1.07 gms.) in propionic acid (10 ml.), containing p-toluenesulfonic acid monohydrate (0.1 gm.) at 0° C, add trifluoroacetic anhydride (4 ml.) dropwise. Allow the reaction mixture to stand at 0° C for 5 minutes, then warm to room temperature and let remain at room temperature for 3 hours. Pour the reaction mixture into water, extract the aqueous mixture with ethyl acetate, wash the combined organic extracts with 5% sodium hydroxide then with water, dry over magnesium sulfate and evaporate to a residue comprising 16-methylene-1,4-pregnadiene-11β,17α,21-triol-3,20-dione 11-trifluoroacetate 17,21-dipropionate.

D. 16-Methylene-1,4,6-Pregnatriene-11β,17α,21-Triol-3,20-Dione 11-Trifluoroacetate 17,21-Dipropionate In a manner similar to that described in Preparation 1A, treat 16-methylene-1,4-pregnadiene-11β,17α,21-triol-3,20-dione 11-trifluoroacetate 17,21-dipropionate with dry hydrogen chloride and DDQ to obtain 16-methylene-1,4,6-pregnatriene-11β,17α,21-triol-3,20-dione 11-trifluoroacetate 17,21-dipropionate.

E. 16-Methylene-1,4,6-Pregnatriene-11β,17α,21-Triol-3,20-Dione 17,21-Dipropionate To a solution of 16-methylene-1,4,6-pregnatriene-11β,17α,21-triol-3,20-dione 11-trifluoroacetate 17,21-dipropionate (0.52 gms.) in methanol (26 ml.) add sodium benzoate (1.5 gms.) and stir at room temperature for 2½ hours. Evaporate the solution in vacuo at room temperature and wash the resultant residue thoroughly with water. Separate the solids by filtration and dry to obtain 16-methylene-1,4,6-pregnatriene-1β,17α,21-triol-3,20-dione 17,21-dipropionate. Additional product is obtained by extracting the combined water washes and filtrate with ethyl acetate, washing the organic extract with water, drying over magnesium sulfate and evaporate to obtain a residue of 16-methylene-1,4,6-pregnatriene-11β,17α,21-triol-3,20-dione 17,21-dipropionate.

PREPARATION 6

3-Oxo-17α-1,4,6-Pregnatriene-21,17β-Carbolactone

To a solution of 3-oxo-17α-4,6-pregnadiene-21,17β-carbolactone (20 gms.) in benzene (600 ml.) and dioxane (600 ml.) add 2,3-dichloro-5,6-dicyanobenzoquinone (DDQ) (80 gms.) and stir the reaction mixture at reflux temperature for 18 hours. Cool the reaction mixture, filter, and evaporate the filtrate in vacuo. Dissolve the resultant residue in a minimum amount of chloroform and place on a column containing 200 gms. of alumina and elute with chloroform (1 liter). Evaporate the eluate in vacuo to a residue comprising 3-oxo-17α-1,4,6-pregnatriene-21,17β-carbolactone. Purify by crystallization from acetone:ethyl ether.

PREPARATION 7

11-Oxygenated-4,6-Pregnadiene-17α,21-Diol-3,20-Diones and Esters Thereof

In the procedures of Preparations 1 and 4, by utilizing as starting compounds the 1,2-dihydro analog corresponding to the 1,4-bis-dehydro analog named therein, there are obtained 1,2-dihydro-4,6-pregnadiene derivatives corresponding to the 1,4,6-pregnatriene products of Preparations 1 and 4 which, when reacted according to the procedure of Preparations 2, 3, and 5, will produce 4,6-pregnadiene derivatives corresponding to the 1,4,6-pregnatriene products named therein.

EXAMPLE 1

7α-Bromo-16α-Methyl-1,4-Pregnadiene-11β,17α,21-Triol-3,20-Dione 17,21-Dipropionate A. Add 16α-methyl-1,4,6-pregnatriene-11β,17,21-triol-3,20-dione 17,21-dipropionate (0.29 gms.) to a solution of 30% (w/v) dry hydrogen bromide in acetic acid (4 ml.) precooled to 0° C. Stir the reaction mixture at 0° C for 1 hour, pour into ice water, separate the resultant solids by filtration, wash the precipitate with water and dry. Purify by triturating with acetone:ether and drying the triturated precipitate to obtain 7α-bromo-16α-methyl-1,4-pregnadiene-11β,17α,21-triol-3,20-dione 17,21-dipropionate, (0.19 gms.).

Alternatively, the compound of this example is prepared according to following procedures 1B and 1C.

B. 7α-Bromo-16α-Methyl-1,4-Pregnadiene-17α,21-Diol-3,11,20-Trione 17,21-Dipropionate:

To a solution of 16α-methyl-1,4,6-pregnatriene-17α,21-diol-3,11,20-trione 17,21-dipropionate (0.5 gms.) in glacial acetic acid (2 ml.), at 0° C, add a solution of dry hydrogen bromide gas (3 gms.) in glacial acetic acid (8 ml.) freshly prepared at 0° C. Stir the reaction mixture for 1 hour at 0° C, pour into ice water (400 ml.), stir for 30 minutes, then separate the resultant precipitate by filtration, wash the precipitate with water until the water washings are neutral, air dry the precipitate to obtain 7α-bromo-16α-methyl-1,4-pregnadiene-17α,21-diol-3,11,20-trione 17,21-dipropionate, (0.51 gms).

C. To a mixture of 7α-bromo-16α-methyl-1,4-pregnadiene-17α,21-diol-3,11,20-trione 17,21-dipropionate (2.84 gms.) and sodium borohydride (0.573 gms.) under an atmosphere of nitrogen at 0° C add methanol (8 ml.) precooled to 0° C and stir the reaction mixture for 5 minutes at 0° C. Pour the reaction mixture into ice water (2 liters) and 1 N hydrochloric acid (300 ml.), separate the resultant precipitate by filtration, wash the precipitate with water and air dry to obtain 7α-bromo-16α-methyl-1,4-pregnadiene-11β,17α,21-triol-3,20-dione 17,21-dipropionate, (2.6 gm). Purify by crystallization from acetone:ether:hexane; m.p. >295° C; $[\alpha]_D^{26}$ + 37.3° (dimethylformamide); $\lambda_{max}^{methanol}$ 242 nm (ε15,350); $\nu_{max}^{nujol}$ 1743, 1735, 1660, 1612, 1600 cm$^{-1}$; nmr (dmso-d$_6$) δ0.85 (C$_{16}$-CH$_3$, d J7Hz), 1.03 (C$_{13}$-CH$_3$, s), 1.43 (C$_{10}$-CH$_3$, s), 4.38 (11α-H, mult.), 4.75 (7β-H, mult.), 4.81 (C$_{21}$-H, s), 5.86 (C$_4$-H, s), 6.19 (C$_9$-H, dd J10,2Hz), 7.31 (C$_1$-H, d J10 Hz), purified yield 1.44 gms.)

EXAMPLE 2

7α-Bromo-16α-Methyl-1,4-Pregnadiene-11β,17α,21-Triol-3,20-Dione 17-Benzoate 21-Acetate A. To 16α-methyl-1,4,6-pregnatriene-11β,17α,21-triol-3,20-dione 17-benzoate 21-acetate (0.31 gms.) add a solution of 30% dry hydrogen bromide in glacial acetic acid (6.2 ml.) at 0° C. Pour into ice water, separate the resultant precipitate by filtration, wash the precipitate with water, and air dry. Purify the precipitate via thin layer chromatography on silica gel using as developing solvent ether:hexane (2:1) and eluting with ethyl acetate the band containing the desired product as shown by ultraviolet light. Evaporate the combined ethyl acetate eluates to a residue comprising 7α-bromo-16β-methyl-1,4-pregnadiene-11β,17α,21-triol-3,20-dione 17-benzoate 21-acetate. Further purify by triturating the residue with isopropyl ether, (0.125 gms.).

Alternatively, the compound of this example is prepared according to following procedures 2B and 2C.

B. 7α-Bromo-16α-Methyl-1,4-Pregnadiene-17α,21-Diol-3,11,20-Trione 17-Benzoate 21-Acetate To a freshly prepared solution of dry hydrogen bromide gas (9.3 gms.) in glacial acetic acid (16 ml.) at 0° C add dropwise a solution of 16α-methyl-1,4,6-pregnatriene-17α,21-diol-3,11,20-trione 17-benzoate 21-acetate (1.56 gms.) in glacial acetic acid (5 ml.). Stir the reaction for 1 hour at 0° C, pour into ice water, stir the aqueous mixture for 30 minutes, then separate the resultant precipitate by filtration, wash the precipitate with water, and air dry to give 7α-bromo-16α-methyl-1,4-pregnadiene-17α,21-diol-3,11,20-trione 17-benzoate 21-acetate (1.6 gms.) Further purify by crystallization from acetone:hexane; m.p. 190°–192.5°; $[\alpha]_D^{26}$ + 77.3° (dimethylformamide); $\lambda_{max}^{methanol}$ 232 nm ($\epsilon$27,600).

C. To a mixture of 7α-bromo-16α-methyl-1,4-pregnadiene-17α,21-diol-3,11,20-trione 17-benzoate 21-acetate (1.05 gms.) and sodium borohydride (0.1 gms.) under an atmosphere of nitrogen at 0° C, add a precooled solution of tetrahydrofuran (7.5 ml.) and methanol (2.5 ml.) and stir the reaction mixture for 25 minutes at 0° C. Pour into ice water (500 ml.) and 1 N hydrochloric acid (100 ml.). Separate the resultant precipitate by filtration, wash the precipitate with water and air dry to obtain 7α-bromo-16α-methyl-1,4-pregnadiene-11β,17α,21-triol-3,20-dione 17-benzoate 21-acetate (0.53 gms.). Further purify by crystallization from acetone:hexane:ether; m.p. 156°–159° C; $[\alpha]_D^{26}$ + 21.1° (dimethylformamide); $\lambda_{max}^{methanol}$ 233 nm ($\epsilon$26,800); nmr (dmso-$d_6$) δ0.89 ($C_{16}$-$CH_3$, d J7Hz), 1.12 ($C_{13}$-$CH_3$, s), 1.48 ($C_{10}$-$CH_3$, s), 2.13 (OAc, s), 4.46 (11α-H, mult.), 4.96 ($C_{21}$-H, quart.), 4.90 (7β-H, mult.), 6.00 ($C_4$-H, s), 6.28 ($C_2$-H, d,d J10,2Hz), 7.39 ($C_1$-H, d, J10Hz), 7.50–8.00 (phenyl, mult.).

EXAMPLE 3

7α-Bromo-11-Oxo- (and 11β-Hydroxy)-1,4-Pregnadiene-17α,21-Diol-3,20-Diones and Esters Thereof A. 11-Oxo- Derivatives In a manner similar to that described in Examples 1B and 2B, treat each of the following 11-oxo-1,4,6-pregnatrienes with dry hydrogen bromide in glacial acetic acid:

the 21-acetate, 21-n-butyrate, 21-isobutyrate, 21-valerate, 21-caprylate, 21-(1'-adamantyl)-carboxylate, 21-(1'-adamantyl)-acetate, 21-benzoate, and 21-p-methoxybenzoate esters of 16α-methyl-1,4,6-pregnatriene-17α,21-diol-3,11,20-trione 17-propionate;

the 21-acetate, 21-n-butyrate, 21-isobutyrate, 21-valerate, 21-caprylate, 21-(1'-adamantyl)-carboxylate, 21-(1'-adamantyl)-acetate, 21-benzoate and 21-p-methoxybenzoate esters of 16α-methyl-1,4,6-pregnatriene-17α,21-diol-3,11,20-trione 17-n-butyrate;

the 21-acetate, 21-n-butyrate, 21-isobutyrate, 21-valerate, 21-caprylate, 21-(1'-adamantyl)-carboxylate, 21-(1'-adamantyl)-acetate, 21-benzoate and 21-p-methoxybenzoate esters of 16α-methyl-1,4,6-pregnatriene-17α,21-diol-3,11,20-trione 17-benzoate;

16α-methyl-1,4,6-pregnatriene-17α,21-diol-3,11,20-trione 17,21-diacetate;

the 21-acetate, 21-propionate and 21-valerate esters of 16α-methyl-1,4,6-pregnatriene-17α,21-diol-3,11,20-trione 17-valerate;

16α-methyl-1,4,6-pregnatriene-17α,21-diol-3,11,20-trione 17-isobutyrate 21-acetate;

and 16α-methyl-1,4,6-pregnatriene-17α,21-diol-3,11,20-trione 17-dodecanoate 21-propionate;

and the 16β-epimers and 16-unsubstituted analogs of the foregoing and the 16-methylene derivatives corresponding to the foregoing.

Isolate and purify each of the resulting products in a manner similar to that described in Examples 1B and 2B to obtain, respectively, the 21-acetate, 21-n-butyrate, 21-isobutyrate, 21-valerate, 21-caprylate, 21-(1'-adamantyl)-carboxylate, 21-(1'-adamantyl)-acetate, 21-benzoate and 21-p-methoxybenzoate esters of 7α-bromo-16α-methyl-1,4-pregnadiene-17α,21-diol-3,11,20-trione 17-propionate;

the 21-acetate, 21-n-butyrate, 21-isobutyrate, 21-valerate, 21-caprylate, 21-(1'-adamantyl)-carboxylate, 21-(1'-adamantyl)-acetate, 21-benzoate and 21-p-methoxybenzoate esters of 7α-bromo-16α-methyl-1,4-pregnadiene-17α,21-diol-3,11,20-trione 17-n-butyrate;

the 21-acetate, 21-n-butyrate, 21-isobutyrate, 21-valerate, 21-caprylate, 21-(1'-adamantyl)-carboxylate, 21-(1'-adamantyl)-acetate, 21-benzoate and 21-p-methoxybenzoate esters 7α-bromo-16α-methyl-17α,21-diol-3,11,20-trione 17-benzoate;

7α-bromo-16α-methyl-1,4-pregnadiene-17α,21-diol-3,11,20-trione 17,21-diacetate;

the 21-acetate, 21-propionate, and 21-valerate esters of 7α-bromo-16α-methyl-1,4-pregnadiene-17α,21-diol-3,11,20-trione 17-valerate;

7α-bromo-16α-methyl-1,4-pregnadiene-17α,21-diol-3,11,20-trione 17-isobutyrate 21-acetate;

and 7α-bromo-16α-methyl-1,4-pregnadiene-17α,21-diol-3,11,20-trione 17-dodecanoate 21-propionate;

and the 16β-epimers and 16-unsubstituted analogs of the foregoing and the 16-methylene derivatives corresponding to the foregoing.

B. 11β-Hydroxy Derivatives

1. In a manner similar to that described in Examples 1A and 2A, treat each of the 11β-hydroxy-7-unsubstituted-1,4,6-pregnatriene derivatives corresponding to each of the 11-oxo-7-unsubstituted-1,4,6-pregnatriene starting compounds of Example 3A with dry hydrogen bromide in acetic acid, and isolate and purify each of the resulting products in a manner similar to that described in Examples 1A and 1B to obtain, respectively, the 21-acetate, 21-n-butyrate, 21-isobutyrate, 21-valerate, 21-caprylate, 21-(1'-adamantyl)-carboxylate, 21-(1'-adamantyl)-acetate, 21-benzoate and 21-p-methoxybenzoate esters of 7α-bromo-16α-methyl-1,4-pregnadiene-11β,17α,21-triol-3,20-dione 17-propionate;

the 21-acetate, 21-n-butyrate, 21-isobutyrate, 21-valerate, 21-caprylate, 21-(1'-adamantyl)-carboxylate, 21-(1'-adamantyl)-acetate, 21-benzoate and 21-p-methoxybenzoate esters of 7α-bromo-16α-methyl-1,4-pregnadiene-11β,17α,21-triol-3,20-dione 17-n-butyrate;

the 21-acetate, 21-n-butyrate, 21-isobutyrate, 21-valerate, 21-caprylate, 21-(1'-adamantyl)-carboxylate, 21-(1'-adamantyl)-acetate, 21-benzoate and 21-p-methoxybenzoate esters of 7α-bromo-16α-methyl-1,4-pregnadiene-11β,17α,21-triol-3,20-dione 17-benzoate;

7α-bromo-16α-methyl-1,4-pregnadiene-11β,17α,21-triol-3,20-dione 17,21-diacetate;

the 21-acetate and 21-valerate esters of 7α-bromo-16α-methyl-1,4-pregnadiene-11β,17α,21-triol-3,20-dione 17-valerate;

7α-bromo-16α-methyl-1,4-pregnadiene-11β,17α,21-triol-3,20-dione 17-isobutyrate 21-acetate;

7α-bromo-16α-methyl-1,4-pregnadiene-11β,17α,21-triol-3,20-dione 17-dodecanoate 21-propionate;

and the 16β-epimers and 16-unsubstituted analogs of the foregoing and the 16-methylene derivatives corresponding to the foregoing.

2. Via Reduction of the 11-Oxo Analog:

Alternatively, the 7α-bromo-11β-hydroxy derivatives of Example 3B(1) are prepared by reducing the corresponding 11-oxo derivative (prepared in Example 3A) with sodium borohydride in tetrahydrofuran and methanol at 0° C under an atmosphere of nitrogen according to the procedure of Example 1C.

EXAMPLE 4

7α-Iodo-16α-Methyl-1,4-Pregnadiene-11β,17α,21-Triol-3,20-Dione 21-Acetate

Add 16α-methyl-1,4,6-pregnatriene-11β,17α,21-triol-3,20-dione 21-acetate (0.1 gms.) to a solution of dry hydrogen iodide (0.512 gms.) in glacial acetic acid (2 ml.) and stir the reaction mixture at room temperature for 50 minutes. Pour into ice water, separate the resultant precipitate by filtration and dry the precipitate. Triturate the precipitate with ether, separate the solid by filtration, dissolve the solid in methylene chloride, wash the methylene chloride solution with aqueous O.1 N sodium thiosulfate solution, then with water, dry over magnesium sulfate and evaporate in vacuo. Triturate the resultant residue with hexane and filter to obtain 7α-iodo-16α-methyl-1,4-pregnadiene-11β,17α,21-triol-3,20-dione 21-acetate, (8 mg.).

B. In similar manner, treat each of the 9-unsubstituted-1,4,6-pregnatriene-3,20-dione intermediates prepared as described in Preparations 1–10 with hydrogen iodide in acetic acid according to the procedure of Example 9A to obtain the corresponding 7α-iodo-9-unsubstituted-1,4-pregnadiene-3,20-dione derivative.

EXAMPLE 5

7α-Chloro-16α-Methyl-1,4-Pregnadiene-11β,17α,21-Triol-3,20-Dione 17,21-Dipropionate A. Add 16α-methyl-1,4,6-pregnatriene-11β,17α,21-triol-3,20-dione 17,21-dipropionate (2.0 gms.) to dioxane (24 ml.) which has been saturated with dry hydrogen chloride gas. Stir at room temperature for 16 hours, pour into ice water (600 ml.), separate the resultant precipitate by filtration, wash the precipitate with water and dry in air. Separate the components in the foregoing precipitate on silica gel via thin layer chromatography utilizing as developing solvent ether:hexane (2:1), and elute with ethyl acetate the band containing 7α-chloro-16α-methyl-1,4-pregnadiene-11β, 17α,21-triol-3,20-dione 17,21-dipropionate as shown by ultraviolet light. Evaporate the combined ethyl acetate eluates and triturate the resultant residue with acetone: ether, then filter and dry the triturated precipitate to obtain 7α-chloro-16α-methyl-1,4-pregnadiene-11β,17α,21-triol-3,20-dione 17,21-dipropionate, (0.33 gms.).

Alernatively, the compound of this Example is prepared according to following procedures 5B and 5C.

B. 7α-Chloro-16α-Methyl-1,4-Pregnadiene-17α,21-Diol-3,11,20-Trione 17,21-Dipropionate Saturate dry tetrahydrofuran (137 ml.) at 0° C with dry hydrogen chloride gas. Add 16α-methyl-1,4,6-pregnatriene-17α,21-diol-3,11,20-trione 17,21-dipropionate (6.85 gms.) and stir the reaction mixture at 0° C for 1 hour. Pour into ice water (1 liter) and stir for ½ hour. Separate the resultant precipitate by filtration, wash with water, and air dry to give 7α-chloro-16α-methyl-1,4-pregnadiene-17α,21-diol-3,11,20-trione 17,21-dipropionate (6.64 gms.). Purify from methanol:acetone containing a trace of propylene oxide; $[\alpha]_D^{26} + 76.2°$ (dimethylformamide); $[M]^+$ 520, 518.

C. To a solution of 7α-chloro-16α-methyl-1,4-pregnadiene-17α,21-diol-3,11,20-trione 17,21-dipropionate (3.2 gms.) in tetrahydrofuran (24 ml.) and methanol (8 ml.) at 0° C under an atmosphere of nitrogen add sodium borohydride (0.697 gms.) and stir the reaction mixture for 15 minutes at 0° C. Pour into ice water (1.8 liters) and 250 ml. of 1 N hydrochloric acid. Separate the resultant precipitate by filtration and air dry to give 7α-chloro-16α-methyl-11β,17α,21-triol-3,20-dione 17,21-dipropionate (2.95 gms.). Purify by crystallizing twice from acetone:methanol:isopropyl ether; m.p. 212°–216° C; $[\alpha]_D^{26} + 42.6°$ (dimethylformamide); $[M]^+$ 522, 520; $\lambda_{max}^{methanol}$ 242 nm ($\epsilon$ = 15,600); $\nu_{max}^{nujol}$ 1743, 1730, 1720, 1652, 1610, 1595 cm$^{-1}$; nmr (dmso-d$_6$) δ 0.84 (C$_{16}$-CH$_3$, d J7Hz), 1.02 (C$_{13}$-CH$_3$, s), 1.42 (C$_{10}$-CH$_3$, s), 4.38 (11α-H, mult.), 4.67 (7β-H, mult.), 4.80 (C$_{21}$-H, s), 5.95 (C$_4$-H, s), 6.20 (C$_2$-H, dd J10,2Hz), 7.35 (C$_1$-H, d J10Hz), purified yield = 1 gm.

EXAMPLE 6

7α-Chloro-11-Oxo-(and 11β-Hydroxy)-1,4-Pregnadiene-17α,21-Diol-3,20-Diones and Esters Thereof A. 11-Oxo Derivatives In a manner similar to that described in Example 5B, treat each of the 11-oxo-1,4,6-pregnatriene starting compounds listed in Example 3A with hydrogen chloride in tetrahydrofuran, then isolate and purify each of the resultant products in a manner similar to that described in Example 5B to obtain, respectively, the 7α-chloro derivatives corresponding to each of the 7α-bromo products listed in Example 3A.

B. 11β-Hydroxy Derivatives

1. In a manner similar to that described in Example 5A, treat each of the 11β-hydroxy-7-unsubstituted-1,4,6-pregnatriene derivatives corresponding to each of the 11-oxo-7-unsubstituted 1,4,6-pregnatriene starting compounds of Example 3A with hydrogen chloride in dioxane and isolate and purify each of the resulting products in a manner similar to that described in Example 5A to obtain, respectively, the 7α-chloro derivatives corresponding to each of the 7α-bromo products listed in Example 3B(1).

2. Via Reduction of the 11-Oxo Analog:

Alternatively, the 7α-chloro-11β-hydroxy derivatives of Example 5B(1) are prepared by reducing the corresponding 11-oxo derivative (prepared in Example 5A) with sodium borohydride in tetrahydrofuran and methanol at 0° C under an atmosphere of nitrogen according to the procedure of Example 1C.

EXAMPLE 7

3-Oxo-7α-Chloro-17α-1,4-Pregnadiene-21,17β-Carbolactone

1. To dry tetrahydrofuran (40 ml.) previously saturated with dry hydrogen chloride gas at 0°–5° C, add 3-oxo-17α-1,4,6-pregnatriene-21,17β-carbolactone (2 gms.) and stir at 0°–5° C for 1 hour. Pour the reaction mixture into ice water (400 ml.) and separate the resultant precipitate by filtration, wash the precipitate with water and dry to obtain 3-oxo-7α-chloro-17α-1,4-pregnadiene-21,17β-carbolactone. Purify by crystallization from acetone:hexane; $[\alpha]_D^{26} + 6.8°$ (dimethylformamide); $\lambda_{max}^{methanol}$ 243 mμ ($\epsilon$ =15,920); m.p. 133°–136° C; (980 mg.).

2. In similar manner, treat each of (17R)-spiro-[1,4,6-androstatriene-17,1'-cyclobutane]-3,2'-dione and 2',3'α-tetrahydrofuran-2'-spiro-17(1,4,6-androstatriene-3-one) with dry hydrogen chloride in tetrahydrofuran at 0.5° C and isolate each of the resultant products in a manner similar to that described to obtain, respectively, (17R)-spiro-[7α-chloro-1,4-androstadiene-17,1'-cyclobutane]-3,2'-dione and 2',3'α-tetrahydrofuran-2'-spiro-17(7α-chloro-1,4-androstadiene-3-one).

EXAMPLE 8

3-Oxo-7α-Bromo-17α-1,4-Pregnadiene-21,17β-Carbolactone

Bubble dry hydrogen bromide (7.5 gms.) into glacial acetic acid (12.5 ml.) at 5°–10° C. Then add a solution of 3-oxo-17α-1,4,6-pregnatriene-21,17β-carbolacetone (1 gm.) in glacial acetic acid. Stir the reaction mixture at 5° C for 45 minutes, then pour into ice water (250 ml.) and separate the resultant precipitate by filtration, wash with water and dry to obtain 3-oxo-7α-bromo-17α-1,4-pregnadiene-21,17β-carbolactone. Purify by crystallization from acetone:hexane:ether; $[\alpha]_D^{26} + 7.7°$ (dimethylformamide); $\lambda_{max}^{methanol}$ 243 mμ ($\epsilon$ =15,100); m.p. 125°–130° C (dec.) (1.2 gms.).

In similar manner, treat each of (17R)-spiro-[1,4,6-androstatriene-17,1'-cyclobutane]-3,2'-dione and 2',3'α-tetrahydrofuran-2'-spiro-17(1,4,6-androstatriene-3-one) with dry hydrogen bromide in glacial acetic acid and isolate each of the resultant products in similar manner to obtain, respectively, (17R)-spiro-[7α-bromo-1,4-androstadiene-17,1'-cyclobutane]-3,2'-dione and 2',3'α-tetrahydrofuran-2'-spiro-17(7α-bromo-1,4-androstadiene-3-one).

EXAMPLE 9

3-Oxo-7α-Iodo-17α-1,4-Pregnadiene-21,17β-Carbolactone

Bubble hydrogen iodide (2.6 gms.) into glacial acetic acid (10 ml.) at 5°–10° C, then add 3-oxo-17α-1,4,6-pregnatriene-21,17β-carbolactone (0.5 gms.) and stir at 5°–10° C for 45 minutes. Pour the reaction mixture into ice water (150 ml.) containing sodium thiosulfatepentahydrate (5 gms.). Separate the resultant precipitate by filtration, wash the precipitate with water and dry in vacuo to obtain 3-oxo-7α-iodo-17α-1,4-pregnadiene-21,17β-carbolactone. Purify by dissolving in a minimum amount of ethyl acetate and separating the components in the foregoing precipitate on silica gel via thin layer chromatography utilizing as developing solvent chloroform:ethyl acetate (1:1) and eluting with a solvent mixture of 15% acetone in ethyl acetate the band containing the desired product as shown by ultraviolet light. Evaporate the combined eluates to a residue comprising 3-oxo-7α-iodo-17α-1,4-pregnadiene-21,17β-carbolactone (1.05 gms.).

In similar manner, treat each of (17R)-spiro-[1,4,6-androstatriene-17,1'-cyclobutane]-3,2'-dione and 2',3'α-tetrahydrofuran-2'-spiro-17(1,4,6-androstatriene-3-one) with dry hydrogen iodide in glacial acetic acid and isolate and purify each of the resultant products in the manner similar to that described to obtain, respectively, (17R)-spiro-[7α-iodo-1,4-androstadiene-17,1'-cyclobutane]-3,2'-dione and 2',3'α-tetrahydrofuran-2'-spiro-17(7α-iodo-1,4-androstadiene-3-one).

EXAMPLE 10

3-Oxo-7α-Chloro-17α-4-Pregnene-21,17β-Carbolactone

To a 7.2% solution of hydrogen chloride in acetic acid (30 ml.) add with stirring 3-oxo-17α-4,6-pregnadiene-21,17β-carbolactone (3 gms.). After 5 minutes pour the reaction mixture into water (500 ml.). Separate the resultant precipitate by filtration, wash the precipitate with water and partially dry under a blanket of nitrogen. Resuspend the precipitate in water, filter, dry the precipitate at room temperature in vacuo to give a residue comprising 3-oxo-7α-chloro-4-pregnene-21,17β-carbolactone in admixture with 3-oxo-17α-4,6-pregnadiene-21,17β-carbolactone, yield 2.83 gms. Dissolve the foregoing precipitate in methanol and separate the components in the foregoing precipitate on silica gel via thick layer chromatography utilizing as developing solvent ethyl acetate:hexane (1:1) and elute with ethyl acetate the band containing 3-oxo-7α-chloro-4-pregnene-21,17β-carbolactone as shown by ultraviolet light. Add methanol to the ethyl acetate eluate and evaporate in vacuo the solvent mixture at a temperature in the range of about 30°–35° C. Add methanol to the resultant mixture and evaporate in vacuo. Add ether and hexane to the resultant residue, and filter the resultant white solid thereby formed to obtain 3-oxo-7α-chloro-17α4-pregnene-21,17β-carbolactone; $\lambda_{max}^{methanol}$ 238 nm ($\epsilon$ = 15,980). Store in an open vessel at room temperature in vacuo.

EXAMPLE 11

3-Oxo-7α-Bromo-17α-4-Pregnene-21,17β-Carbolactone

Add 3-oxo-17α-4,6-pregnadiene-21,17β-carbolactone (100 mg.) to a 30–35% solution of hydrobromic acid in acetic acid (2 ml.) at 15°–20° C. Stir for 5 minutes, then pour the reaction mixture into ice water, filter the resultant precipitate, wash the filtrate with water, then partially dry the filtrate under a nitrogen stream. Dissolve in methanol and separate the components in the foregoing precipitate on silica gel via thick layer chromatography utilizing as developing solvent ethyl acetate:hexane (1:1) and elute with ethyl acetate the band containing 3-oxo-7α-bromo-17α-4-pregnene-21,17β-carbolactone as shown by ultraviolet spectrunm. To the ethyl acetate eluate add methanol until the ratio of ethyl acetate to methanol is in the range of 5–10:1. Evaporate the solvent mixture in vacuo, then add ether:hexane to the resultant residue and filter the resultant precipitate to give 3-oxo-7α-bromo-17α-4-pregnene-21,17β-carbolactone. Store in an open vessel in vacuo at room temperature.

EXAMPLE 12

7α-Chloro-4-Pregnene-17α,21-Diol-3,11,20-Trione 17,21-Dipropionate and the 16α-Methyl and 16β-Methyl Analogs Thereof A. Dissolve 4,6-pregnadiene-17α,21-diol-3,11,20-trione 17,21-dipropionate (911 mg.) in a freshly prepared solution of hydrogen chloride in tetrahydrofuran and water (10° C) (10 ml.), comprising 38.2% by weight of hydrogen chloride and 3.7% by weight of water. Stir the reaction mixture for 15 minutes at 0°–2° C, then pour into ice water (100 ml.). Separate the resultant precipitate by filtration, wash the precipitate with water, partially dry under a blanket of nitrogen, then dry at room temperature in vacuo for 17 hours to obtain 7α-chloro-4-pregnene-17α,21-diol-3,11,20-trione 17,21-dipropionate in admixture with 4,6-pregnadiene-17α,21-diol-3,11,20-trione 17,21-dipropionate. Dissolve the foregoing precipitate in acetone and separate the components therein on silica gel via thick layer chromatography developing with hexane:dimethoxyethane (2:1), and elute with ethyl acetate the band containing 7α-chloro-4-pregnene-17α,21-diol-3,11,20-trione 17,21-dipropionate as shown by ultraviolet spectrum. Evaporate the ethyl acetate eluate at room temperature and crystallize the resultant residue from acetone:hexane at room temperature to obtain 7α-chloro-4-pregnene-17α,21-diol-3,11,20-trione 17,21-dipropionate. Store in an open vessel at room temperature in vacuo.

B. Treat each of 16α-methyl-4,6-pregnadiene-17α,21-diol-3,11,20-trione 17,21-dipropionate and 16β-methyl-4,6-pregnadiene-17α,21-diol-3,11,20-trione 17,21-dipropionate with hydrogen chloride in aqueous tetrahydrofuran and isolate each of the resultant products in a manner similar to that described in above Example 12A to obtain, respectively, 7α-chloro-16α-methyl-4-pregnene-17α,21-diol-3,11,20-trione 17,21-dipropionate and 7α-chloro-16β-methyl-4-pregnene-17α,21-diol-3,11,20-trione 17,21-dipropionate.

EXAMPLE 13

7α-Bromo-4-Pregnene-17α,21-Diol-3,11,20-Trione-17,21-Dipropionate and the 16α-Methyl and 16β-Methyl Derivatives Thereof A. Dissolve at room temperature 4,6-pregnadiene-17α,21-diol-3,11,20-trione 17,21-dipropionate (235 mg.) in a freshly prepared solution of hydrogen bromide in acetic acid (44%, 2.5 ml.). Stir at room temperature for 30 minutes, then add the reaction mixture to water (100 ml.), separate the resultant precipitate by filtration, wash with water, dry under a blanket of nitrogen to obtain a mixture comprising 7α-bromo-4-pregnene-17α,21-diol-3,11,20-trione 17,21-dipropionate in admixture with 4,6-pregnadiene-17α,21-diol-3,11,20-trione 17,21-dipropionate. Separate the resultant mixture and purify the desired product in a manner similar to that described in Example 12A to obtain 7α-bromo-4-pregnene-17α,21-diol-3,11,20-trione 17,21-dipropionate. Store in an open vessel at room temperature in vacuo.

B. Treat each of 16α-methyl-4,6-pregnadiene-17α,21-diol-3,11,20-trione 17,21-dipropionate and 16β-methyl-4,6-pregnadiene-17α,21-diol-3,11,20-trione 17,21-dipropionate with hydrogen bromide in acetic acid in the manner described in the manner described in Example 13A, and isolate and purify each of the resultant products in the described manner to obtain 7α-bromo-16α-methyl-4-pregnene-17α,21-diol-3,11,20-trione 17,21-dipropionate and 7α-bromo-16β-methyl-4-pregnene-17α,21-diol-3,11,20-trione 17,21-dipropionate, respectively.

EXAMPLE 14

7α-Halogeno-4-Pregnene-11β,17α,21-Triol-3,20-Dione 17,21-Dipropionate and the 16α-Methyl and 16β-Methyl Derivatives Thereof A. 7α-Chloro-4-Pregnene-11β,17α,21-Triol-3,20-Dione 17,21-Dipropionate and the 16α-Methyl and 16β-Methyl Derivatives Thereof 1. At room temperature dissolve 7α-chloro-4-pregnene-17α,21-diol-3,11,20-trione 17,21-dipropionate (3.1 g.) in methanol (375 ml.) and add water (30 ml.). To this solution at 0°–2° C under an atmosphere of nitrogen add sodium borohydride (2.38 gms.). After 30 minutes, cautiously add the reaction solution to 4.2 liters of water containing 80 ml. of 1 N hydrochloric acid. Isolate the resulting 7α-chloro-11β-hydroxy-pregnene precipitate by filtration, then chromatograph the precipitate over silica gel eluting with chloroform:ethyl acetate (3:1). Evaporate the combined eluates in vacuo. To 152 mg. of the resultant residue, add a suspension of manganese dioxide (600 mg.) in benzene (7 ml.), stir for 5 hours, filter and chromatograph the benzene filtrate on silica gel via thin layer chromatography developing with chloroform:ethyl acetate (3:1) and eluting with ethyl acetate the band containing the desired product as determined by ultraviolet spectrum. Evaporate the ethyl acetate solution in vacuo to a residue comprising 7α-chloro-4-pregnene-11β,17α,21-triol-3,20-dione 17,21-dipropionate. Further purify by crystallization from ether:hexane at room temperature; $\lambda_{max}^{methanol}$ 237 nm ($\epsilon = 15,500$).

2. In a manner similar to that described in Exampl 14A(1), treat each of 6α-chloro-16α-methyl-4-pregnene-17α,21-diol-3,11,20-trione 17,21-dipropionate and 7α-chloro-16β-methyl-4-pregnene-17α,21-diol-3,11,20-trione 17,21-dipropionate with sodium borohydride in aqueous methanol followed by isolation and purification of the 7α-chloro-11β-hydroxy-pregnene thereby produced followed by treatment thereof with manganese dioxide in benzene, thence isolation and purification in the described manner to obtain, respectively, 7α-chloro-16β-methyl-4-pregnene-11β,17α,21-triol-3,20-dione 17,21-dipropionate and 7α-chloro-16β-methyl-4-pregnene-11β,17α,21-triol-3,20-dione 17,21-dipropionate.

B. 7α-Bromo-4-Pregnene-11β,17α,21-Triol-3,20-Dione 17,21-Dipropionate and the 16α-Methyl and 16β-Methyl Derivatives Thereof In the procedures described in Example 14A, by starting with a 7α-bromo derivative corresponding to the 7α-chloro starting compounds named therein, there is obtained the corresponding 7α-bromo-11β-hydroxy-4-pregnene derivatives, namely, 7α-bromo-4-pregnene-11β,17α,21-triol-3,20-dione 17,21-dipropionate and the 16α-methyl and 16β-methyl derivatives thereof.

EXAMPLE 15

Other 7α-Halogeno-11-Oxygenated-4-Pregnene-17α,21-Diol-3,20-Diones and Ester Derivatives Thereof In the procedures of Examples 12 and 13, by starting with other 3,11,20-trioxo-4,6-pregnadiene-17α,21-dihydroxy esterified derivatives prepared as described in Preparation 7, there is obtained 7α-chloro and 7α-bromo-11-oxo-4-pregnene derivatives corresponding to the 1,4-pregnadiene products named in Examples 12 and 13 which, when treated in the manner described in Example 14, yields 7α-halogeno-11β-hydroxy-4-pregnene derivatives corresponding to the 7α-halogeno-11β-hydroxy-1,4-pregnadiene derivatives named therein.

We claim:

1. The process for the preparation and isolation of a 3-oxo-6,9-di-unsubstituted-7α-halogeno-4-dehydro steroid of the pregnane and androstane-17-spirolactone series wherein said halogen has an atomic weight greater than 20, and wherein said 17-spirolactone is defined by one of following formula I and II:

V being oxygen or hydrogen;

which comprises the reaction of a 3-oxo-6,7,9-triunsubstituted-4,6-bis-dehydro steroid of the pregnane and androstane-17-spirolactone series with at least an equimolar quantity of the corresponding hydrogen halide in a non-reactive, organic solvent at temperatures no higher than about 30° C and thence isolation of the 3-oxo-6-unsubstituted-7α-halogeno-4-dehydro steroid thereby formed at temperatures no higher than about 25° C by removing any excess acid and said solvent without subjecting said 3-oxo-6,9-di-unsubstituted-7α-halogeno-4-dehydro steroid to a basic medium, so as to obtain said 3-oxo-6,9-di-unsubstituted-7α-halogeno-4-dehydro steroid substantially free of acid or base.

2. The process of claim 1 wherein there is at least a 5 molar excess of hydrogen halide per mole of steroid and wherein the reaction temperature is in the range of from about 0° to about 20° C.

3. The process of claim 1 wherein the reaction temperature is in the range of from about 0° to about 20° C, wherein said non-reactive, organic solvent is dioxane or tetrahydrofuran, and wherein said hydrogen halide is hydrogen chloride in at least a 10 to 50 molar excess per mole of steroid.

4. The process of claim 1 wherein the reaction temperature is in the range of from about 0° to about 20° C, wherein said non-reactive, organic solvent is a lower alkanoic acid and wherein said hydrogen halide is hydrogen bromide in at least 10–50 molar excess per mole of steroid.

5. The process of claim 4 wherein said lower alkanoic acid is acetic acid.

6. The process of claim 3 wherein said 3-oxo-6,7,9-tri-unsubstituted-4,6-bis-dehydro steroid is a 3-oxo-6,7,9-tri-unsubstituted-1,4,6-pregnatriene of the corticoid series, wherein said non-reactive, organic solvent is tetrahydrofuran and wherein the molar quantity of said hydrogen chloride is about 40 per mole of steroid.

7. The process of claim 6 wherein said 3-oxo-6,7,9-tri-unsubstituted-1,4,6-pregnatriene is a compound of the following formula I:

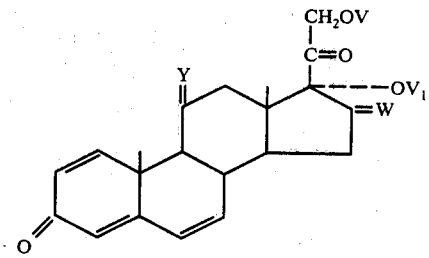

wherein
Y is oxo or (H,βOH);
W is (H,H); (H,CH₃) or =CH₂;
V and V₁ are each hydrogen or an acyl radical of a hydrocarboncarboxylic acid having up to 12 carbon atoms; and
wherein the reaction temperature is at about 0° C;
whereby is isolated a 3-oxo-7α-chloro-1,4-pregnadiene of formula II:

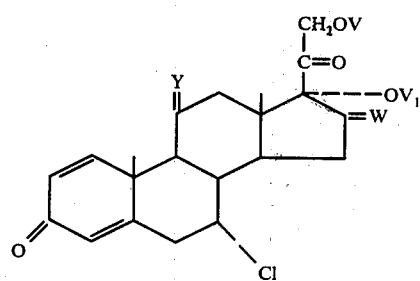

wherein Y, W, V and V₁ are as hereinbefore defined.

8. The process of claim 7 wherein said 3-oxo-6,7,9-tri-unsubstituted-1,4,6-pregnatriene is 16α-methyl-1,4,6-pregnatriene-11β,17α,21-triol-3,20-dione 17,21-dipropionate whereby is isolated 7α-chloro-16α-methyl-1,4-pregnadiene-11β,17α,21-triol-3,20-dione 17,21-dipropionate.

9. The process of claim 4 wherein said 3-oxo-6,7,9-tri-unsubstituted-4,6-bis-dehydro steroid is a 3-oxo-6,7,9-tri-unsubstituted-1,4,6-pregnatriene of the corticoid series and wherein the molar quantity of said hydrogen bromide is about 40 per mole of steroid.

10. The process of claim 9 wherein said 3-oxo-6,7,9-tri-unsubstituted-1,4,6-pregnatriene is a compound of the following formula I:

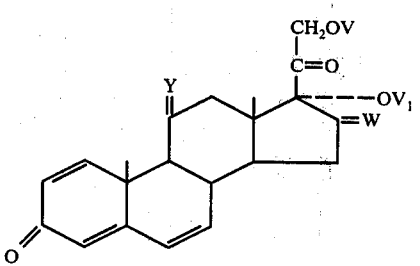

wherein
Y is oxo or (H,βOH);
W is (H,H); (H,CH₃) or =CH₂;
V and V₁ are each hydrogen or an acyl radical of a hydrocarboncarboxylic acid having up to 12 carbon atoms;
wherein said lower alkanoic acid is acetic acid; and wherein the reaction temperature is at about 0° C;
whereby is isolated a 3-oxo-6,9-di-unsubstituted-7α-bromo-1,4-pregnadiene of formula II:

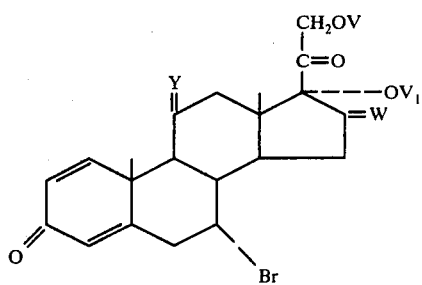

wherein Y, W, V and V₁ are as hereinabove defined.

11. The process of claim 10 wherein said 3-oxo-6,7,9-tri-unsubstituted-1,4,6-pregnatriene is 16α-methyl-1,4,6-pregnatriene-11β,17α,21-triol-3,20-dione 17-benzoate 21-acetate whereby is obtained 7α-bromo-16α-methyl-1,4-pregnadiene-11β,17α,21L -triol-3,20-dione 17-benzoate 21-acetate.

12. The process of claim 3 wherein said 3oxo-6,7,9-tri-unsubstituted-1,2-dihydro-4,6-bis-dehydro steroid of the pregnane series is a compound of the following formula I:

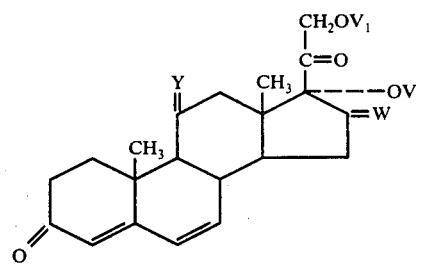

wherein
Y is oxo or (H,βOH);
W is (H,H) (H,CH₃) or =CH₂;
V and V₁ are each hydrogen or an acyl radical of a hydrocarboncarboxylic acid having up to 12 carbon atoms;
whereby is isolated a 3-oxo-6,9-di-unsubstituted-7α-chloro-1,2-dihydro-4-dehydro steroid of formula II:

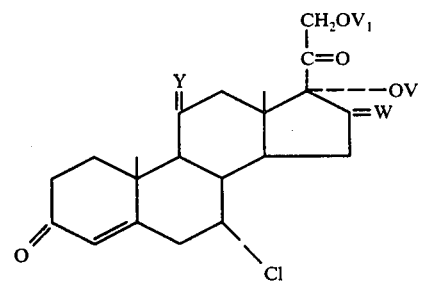

wherein Y, W, V and V₁ are as hereinabove defined.

13. The process of claim 4 wherein said 3-oxo-6,7,9-tri-unsubstituted-4,6-bis-dehydro steroid is a 3-oxo-6,7,9-tri-unsubstituted-1,2-dihydro-4,6-bis-dehydro steroid of the pregnane series having the following formula I:

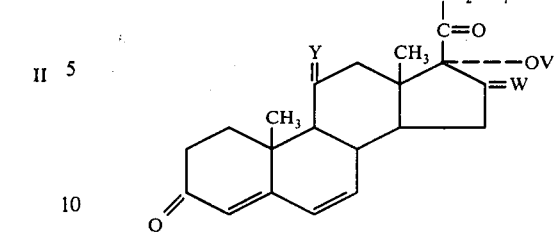

wherein
Y is oxo or (H,βOH);
W is (H,H); (H,CH₃) or =CH₂;
V and V₁ are each hydrogen or an acyl radical of a hydrocarboncarboxylic acid having up to 12 carbon atoms;
whereby is isolated a 3-oxo-6,9-di-unsubstituted-7α-bromo-1,2-dihydro-4-dehydro steroid of formula II:

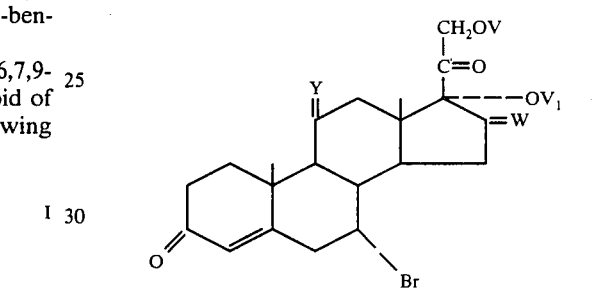

wherein Y, W, V and V₁ are as hereinbefore defined.

14. A 7α-halogeno-4-pregnene-3,20-dione of following formula:

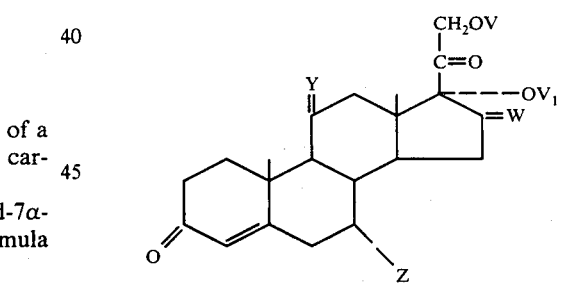

wherein
Y is oxo or (H,βOH);
W is (H,H); (H,CH₃) or =CH₂;
V and V₁ are each hydrogen or an acyl radical of a hydrocarboncarboxylic acid having up to 12 carbon atoms, and Z is a halogen having an atomic weight greater than 20.

15. A compound of claim 14 wherein Z is chlorine or bromine.

16. A compound of claim 14 which is 7α-chloro-4-pregnene-11β,17α,21-triol-3,20-dione 17,21-dipropionate.

17. 3-Oxo-7α-halogeno-17α-4-pregnene-21,17β-carbolactone wherein said halogeno is chlorine or bromine.

18. The process of claim 1 wherein said 3-oxo-6,7,9-tri-unsubstituted-4,6-bis-dehydro steroid of the spirolactone series is a member selected from the group consisting of 3-oxo-17α-4,6-pregnadiene-21,17β-carbolactone, 3-oxo-17α-1,4,6-pregnatriene-21,17β-carbolactone, (17R)-spiro-[1,4,6-androstatriene-17,1'-cyclobutane]-3,2'L -dione and 2',3'α-tetrahydrofuran-2'-spiro-17(1,4,6-androstatriene-3-one);

whereby is isolated a 3-oxo-6-unsubstituted-7α-halogeno-4-dehydro steroid of the spirolactone series selected from the group consisting of 3-oxo-7α-halogeno-17α-4-pregnene-21,17β-carbolactone, 3-oxo-7α-halogeno-17α-1,4-pregnadiene-21,17β-carbolactone, (17R)-spiro-[7αL-bromo-1,4-androstadiene-17,1'-cyclobutane]-3,2'-dione and 2',3'α-tetrahydrofuran-2'-spiro-17(7α-bromo-1,4-androstadiene-3-one), respectively.

* * * * *

UNITED STATES PATENT OFFICE
CERTIFICATE OF CORRECTION

Patent No. 4,076,708                    Dated February 28, 1978

Inventor(s) Michael J. Green et al

It is certified that error appears in the above-identified patent and that said Letters Patent are hereby corrected as shown below:

Column 9, line 64, "-21,17α-carbolac-" should read ---21,17β-carbolactone---. Column 11, line 6, "then pour with aqueous" should read ---then pour into a 0.1 N hydrochloric acid solution (550 ml.). Extract the aqueous mixture with ethyl acetate, wash the organic extracts with aqueous---. Column 13, line 9, "Acids Ester" should read ---Acid Esters---. Column 14, line 24, "the 16α-methyl-" (1st occurrence) should read ---the 16β-methyl---. Column 17, line 4, "-bromo-16β-methyl-" should read ---bromo-16α-methyl---. Column 24, line 36, "of 6α-chloro-" should read ---of 7α-chloro---; line 45, "-chloro-16β-methyl-" should read ---chloro-16α-methyl---. Column 27, line 22, "-11β,17α,21L-triol-" should read ---11β,17α, 21-triol---. Column 29, line 3, "-3,2'L-dione-" should read ---3,2'-dione---. Column 30, line 3, "-/ 7αL-bromo-" should read ---/ 7α-bromo---.

Signed and Sealed this

Twelfth Day of December 1978

[SEAL]

Attest:

RUTH C. MASON
Attesting Officer

DONALD W. BANNER
Commissioner of Patents and Trademarks